United States Patent

Bernáth et al.

Patent Number: 4,623,647
Date of Patent: Nov. 18, 1986

[54] [1,3]OXAZINO[4,3-A]-ISOQUINOLINE DERIVATIVES AND PHARMACEUTICAL COMPOSITIONS CONTAINING THEM

[75] Inventors: Gábor Bernáth; Jenö Kóbor; Ferenc Fölöp, all of Szeged; Pal Sohár, Harmatcsepp; Pál Perjési, Pecs; Elemér Ezer, Budapest; György Hajós, Budapest; Éva Pálosi, Budapest; László Denes, Budapest; László Szporny, Budapest, all of Hungary

[73] Assignee: Richter Gedeon Vegyeszeti Gyar R.T., Budapest, Hungary

[21] Appl. No.: 664,844

[22] Filed: Oct. 25, 1984

[30] Foreign Application Priority Data

Oct. 25, 1983 [HU] Hungary .................................. 3654

[51] Int. Cl.[4] .................. A61K 31/535; C07D 265/34
[52] U.S. Cl. .................................. 514/228; 514/233; 514/239; 544/71; 544/89
[58] Field of Search .................... 544/89, 71; 514/228, 514/233, 239

[56] References Cited

PUBLICATIONS

Grabb et al, Chemical Society Journal, Perkin II (1977) pp. 370–378.

Primary Examiner—Richard L. Raymond
Attorney, Agent, or Firm—Keil & Weinkauf

[57] ABSTRACT

The invention relates to new [1,3]oxazino[4,3-a]-isoquinoline derivatives of the formula (I)

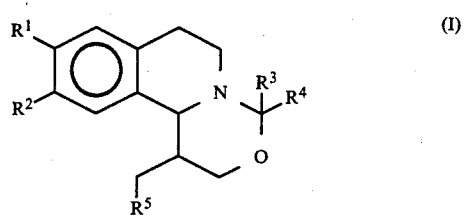

wherein
$R^1$ and $R^2$ represent hydroxyl or alkoxy having from 1 to 6 carbon atoms,
$R^3$ is hydrogen, alkyl having from 1 to 8 carbon atoms, cycloakyl or cycloalkenyl having from 3 to 6 carbon atoms, optionally substituted phenyl, aralkyl having from 1 to 4 carbon atoms in the alkyl moiety or heteroaryl,
$R^4$ is hydrogen or alkyl having from 1 to 4 carbon atoms, or
$R^3$ and $R^4$ together form a $-(CH_2)_n-$ group, in which n is an integer from 3 to 7,
$R^5$ is hydroxyl, halogen or an

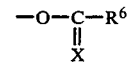

group, in which
$R^6$ is optionally substituted phenyl,
X is oxygen or sulfur,
and salts thereof.

According to another aspect of the invention there is provided a process for the preparation of these compounds. Compounds of formula (I) are pharmaceutically active. Pharmaceutical compositions containing them are also within the scope of the invention.

7 Claims, No Drawings

[1,3]OXAZINO[4,3-A]-ISOQUINOLINE DERIVATIVES AND PHARMACEUTICAL COMPOSITIONS CONTAINING THEM

The invention relates to new [1,3]oxazino-[4,3-a]isoquinoline derivatives of the formula (I)

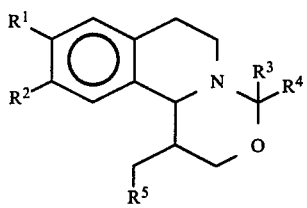

wherein
$R^1$ and $R^2$ represent hydroxyl or alkoxy having from 1 to 6 carbon atoms,
$R^3$ is hydrogen, alkyl having from 1 to 8 carbon atoms, cycloalkyl or cycloalkenyl having from 3 to 6 carbon atoms, optionally substituted phenyl, aralkyl having from 1 to 4 carbon atoms in the alkyl moiety or heteroaryl,
$R^4$ is hydrogen or alkyl having from 1 to 4 carbon atoms, or
$R^3$ and $R^4$ together form a —(CH$_2$)$_n$— group, in which n is an integer from 3 to 7,
$R^5$ is hydroxyl, halogen or an

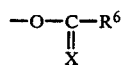

group, in which
$R^6$ is optionally substituted phenyl,
X is oxygen or sulfur,
and salts thereof.

According to another aspect of the invention there is provided a process for the preparation of compounds of formula (I), in which the substituents have the same meanings as defined above, and salts thereof. According to the invention a compound of the formula (II),

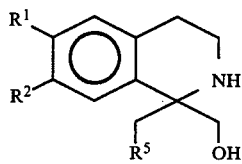

wherein
$R^1$, $R^2$ and $R^5$ are as defined above, or an acid addition salt thereof is reacted with a compound of the formula (III),

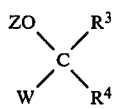

wherein
$R^3$ and $R^4$ are as defined above,
Z is alkyl having from 1 to 4 carbon atoms or acyl,
W is alkoxy having from 1 to 4 carbon atoms, acyloxy or hydrogen, or Z and W together form a second valency bond,
to yield a corresponding compound of formula (I).

In the compounds of formula (I) the groups $R^1$ and/or $R^2$ and/or $R^5$ can be converted into other substituents within the definition of $R^1$, $R^2$ and $R^5$, respectively. If desired, compounds of the formula (I) may be converted into their acid addition salts or can be deliberated therefrom.

Compounds of the formula (I) are biologically active, more particularly show, for example, immunsuppressive, antidepressive, analgesic, antipyretic or gastric acid secretion inhibiting activity.

The term "alkyl" as such or as part of other groups is used in the above definitions to refer to straight-chained or branched alkyl groups, e.g. methyl, ethyl, n-propyl, isopropyl, n-butyl, isobutyl, sec.-butyl, tert.-butyl, n-pentyl, isopentyl, n-hexyl, isohexyl, etc. groups, taking into account the limitations given for the number of carbon atoms.

The term "aralkyl having from 1 to 4 carbon atoms in the alkyl moiety" in the definition of $R^3$ preferably represents a $C_{1-4}$-alkyl-phenyl group, more preferably benzyl or phenylethyl.

Preferred representatives of the cycloalkyl and cycloalkenyl groups in the definition of $R^3$ are e.g. cyclohexyl and cyclohexenyl, respectively.

In the definition of $R^3$ the phenyl group may optionally be substituted by one or more, identical or different substituents, preferably selected from the group consisting of halogen, alkoxy having from 1 to 4 carbon atoms and nitro.

The compounds of the formula (II) used as starting compounds in the process according to the invention are new. Their preparation is disclosed in our co-pending Hungarian patent application Nos. 3651/83 and 3652/83, which correspond respectively to U.S. application Ser. Nos. 664,842 and 664,770. More particularly, compounds of formula (II), in which $R^5$ is hydroxyl, may be prepared by reacting the corresponding 1-methyl-3,4-dihydroisoquinoline or 1-($\beta$-hydroxyethyl)-3,4-dihydroisoquinoline derivatives with formaldehyde, or the hydrate or trimeric derivatives thereof, preferably in alkaline medium, and hydrogenating the compounds obtained. The other compounds of the formula (II) are generally prepared from the compounds containing hydroxyl in place of $R^5$ by conventional reactions.

Compounds of the formula (III) are known, commercially available substances or can be prepared in a known manner. Their preferred representatives are encompassed by the formula (III/1),

in which $R^3$ and $R^4$ are as hereinbefore defined.

The process according to the invention is preferably carried out in an inert organic solvent, preferably an aliphatic alcohol having from 1 to 6 carbon atoms, e.g. methanol or ethanol, or an aromatic hydrocarbon, e.g. benzene. The reaction is preferably performed in the presence of a catalytic amount of an acid, e.g. hydrogen chloride or acetic acid.

The reaction temperature may be varied within wide limits, but is preferably between room temperature and reflux temperature. Most preferably, the reaction is carried out under reflux. The reaction time is a function of the reaction temperature and other reaction conditions, e.g. reactants and the medium employed.

Compounds of analogous structure were published by W. Schneider and K. Schilken [Arch. Pharm. 299,997 (1966)], and were prepared by reacting homocalicotomin with appropriate oxo-compounds. Crabb et al. carried out the cyclization of 1-(β-hydroxyethyl)-1,2,3,4-tetrahydroisoquinoline with formaldehyde and p-nitro-benzaldehyde under similar conditions [Org. Magn. Res. 8, 258 (1976); J. Chem. Soc. Perkin II, 370 (1977)]. The cited articles reported, however, no pharmaceutical activity of the compounds disclosed.

Compounds of the formula (I) can be converted into their acid addition salts by reaction with suitable acids. For this purpose pharmaceutically acceptable acids are preferred.

Salt formation can be carried out, for example, in an inert organic solvent such as a $C_{1-6}$ aliphatic alcohol in such a way that the compound of the formula (I) is dissolved in the solvent and the selected acid or a solution thereof formed with the same solvent is added to the first solution until it becomes slightly acidic (pH 5 to 6). Thereafter the acid addition salt separates and can be removed from the reaction mixture e.g. by filtration.

The compounds of the formula (I) or the salts thereof can be subjected, if desired, to further purification, e.g. recrystallization. The solvents used for recrystallization are selected depending on the solubility and crystallization properties of the compound to be crystallized.

If desired, compounds of the formula (I) obtained in the form of a salt may be converted into the corresponding free compounds in a known manner.

As mentioned before, in the compounds of formula (I) $R^1$ and/or $R^2$ and/or $R^5$ may be converted into other groups falling under the definition given hereinbefore. For example compounds of the formula (I), in which $R^1$ and/or $R^2$ are hydroxyl, can be converted into the corresponding compounds of formula (I), in which $R^1$ and/or $R^2$ represent an alkoxy group having from 1 to 6 carbon atoms by methods known in the art. The 6,7-dimethoxy compounds are most expediently prepared by methylation of the corresponding 6,7-dihydroxy compounds with diazomethane or dimethyl sulfate. The higher ethers can be prepared for example by the Williamson synthesis, using alkyl iodides. On the other hand, from compounds of the formula (I), in which $R^1$ and/or $R^2$ represent an alkoxy group having from 1 to 6 carbon atoms, the corresponding compounds containing hydroxyl as $R^1$ and/or $R^2$ can be obtained by known reactions, e.g. heating with hydrogen iodide or by means of anhydrous aluminium chloride. Compounds, in which $R^5$ is hydroxyl, can be prepared for example from the corresponding halogen derivatives, while the group

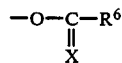

can be introduced also subsequently, by any of the acylating reactants suitable for the introduction of this group.

The new compounds of the formula (I) and their physiologically acceptable salts may be formulated for therapeutic purposes. The invention therefore relates also to pharmaceutical compositions comprising as active ingredient at least one compound of formula (I) or a physiologically acceptable salt thereof, in association with a pharmaceutical carrier or excipient. Carriers conventional for this purpose and suitable for parenteral or enteral administration as well as other additives may be used.

As carriers solid or liquid compounds, for example water, gelatine, lactose, milk sugar, starch, pectin, magnesium stearate, stearic acid, talc, vegetable oils, such as peanut oil, olive oil, arabic gum, polyalkylene glycols, and Vaseline (registered Trade Mark), can be used. The compounds can be formulated as conventional pharmaceutical formulations, for example in a solid (globular and angular pills, dragees, capsules, e.g. hard gelatine capsules) or liquid (injectable oily or aqueous solutions or suspensions) form. The quantity of the solid carrier can be varied within wide ranges, but preferably is between 25 mg and 1 g. The compositions optionally contain also conventional pharmaceutical additives, such as preserving agents, wetting agents, salts for adjusting the osmotic pressure, buffers, flavouring and aroma substances. The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For the pharmacological tests CFLP/LATI/mice of both sexes, weighing 18 to 22 g each and male Han. Wistar/LATI/rats weighing 160 to 180 g each were used. The test materials were administered orally, in 30 mg/kg doses, in the form of a suspension containing 5% of Tween 80, one hour before the tests.

Test Methods

1. Maximum electroshock (mice)

The shock was applied through a corneal electrode (20 mA, 0.2 msec, HSE Schockgerät typ. 207). The animals which do not show a tonic, extensoric spasm as a result of electroshock treatment are considered protected (see Swinyard et al.: J. Pharmacol. Exp. Ther. 106, 319/1952/).

2. Metrazole spasm (mice)

After pretreatment, the animals were administered 125 mg/kg of pentylenetetrazole subcutaneously. The animals, which did not show (a) a clonic, (b) a tonic extensoric spasm and which survived the experiment, were regarded protected. Observation time: one hour (Everett L. M. and Richards R. K.: J. Pharmacol. Exp. Ther. 81, 402/1944/).

3. Inhibition of tetrabenazine catalepsy

The test was carried out on male rats each weighing 160 to 180 g. The test materials were administered intraperitoneally, in a dose of 30 mg/kg, one hour before tetrabenazine administration. The animals, which if their forlegs were placed on a 7 cm high pillar, did not correct their bizarre position within 30 seconds, were regarded cataleptic (Delay J. and Denicker P.: Compt. Rend. Congr. Med. Alenistens Neurologists 19, 497/Luxemb./).

4. Analgesic activity (mice)

One hour after pretreatment, mice were administered 0.4 ml of a 0.6% acetic acid solution intraperitoneally, as a pain stimulus. The frequency of writhing syndrom is registered for 30 minutes. The changes observed as a result of treatment with the test compounds are related to the mean value of the frequency of writhing syndrom in the control group, and the difference is expressed in percentage (Koster R. et al.: Exp. Ther. 72, 74/1941/).

5. Antipyretic activity (rats)

Hyperthermy is induced in rats with Brewer's yeast suspension (0.5% of Brewer's yeast, 1% of arabic gum in a volume of 0.3 ml, s.c.). The animals are treated with the test materials 4 hours later, and the tracheal temperature of the animals is registered with an ELAB thermometer (typ. TE-3) for 4 hours. The antipyretic activity is expressed in percentage of the animals which have an at least one centigrade lower temperature than the average of the control group treated with the solvent (Nimegeers C. J. E. et al.: Arzneimittel Forsch. 25:15/9/1975/).

6. Acute alcoholic intoxication

Male rats each weighing 160 to 180 g were treated with 30 mg/kg doses of the test materials and, after one hour, with 3.5 mg/kg of ethanol, intraperitoneally. The narcosis time of the animals was registered.

The results show that 1-(hydroxymethyl)-4-(4-pyridyl)-8,10-diethoxy-1,6,7,11b-tetrahydro-2H,4H[1,3]oxazino[4,3-a]isoquinoline dihydrochloride (Compound A) or 1-(hydroxymethyl)-4-(phenylethyl)-9,10-dimethoxy-1,6,7,11b-tetrahydro-2H,4H[1,3]oxazino[4,3-a]isoquinoline hydrochloride (Compound B) are about 2 to 3-times more potent analgesic agents than Na-salycilate used as a reference substance (Table I). The Compound B, in addition to its analgesic activity, decreases significantly the acute alcoholic intoxication (Table II).

TABLE I

| Substances | Antispasm activity max. electro-shock | Antispasm activity metrazole a b | Antitetra-benazine activity (%) | Analgesic activity (%) | Antipyretic activity (%) |
| --- | --- | --- | --- | --- | --- |
| Compound A | — | — 24.0× | 40.0 | 30.0× | 20.0 |
| Compound B | — | — 20.0 | 20.0 | 50.0× | 20.0 |
| Na-salycilate | — | — 20.0 | — | 113.0× | 110.0× |

— = ineffective
× = $ED_{50}$ mg/kg p.o.

TABLE II

| Substances | Alcoholic narcosis time min. ($\bar{x} \pm SE$) | (%) |
| --- | --- | --- |
| Solvent | 113.2 ± 10.41 | — |
| Compound B | 66.8 ± 8.11 | 41 |

The animals were treated with a 10 mg/kg oral dose of Compound B one hour before the addition of 3.5 g/kg of ethanol.

The invention is elucidated in detail by the aid of the following non-limiting Examples.

EXAMPLE 1

Preparation of 1-(hydroxymethyl)-9,10-dimethoxy-1,6,7,11b-tetrahydro-2H,4H-[1,3]oxazino[4,3-a]isoquinoline A suspension of 6 mmoles (1.6 g) of 1-[bis(hydroxymethyl)-methyl]-6,7-dimethoxy-1,2,3,4-tetrahydroisoquinoline in 50 ml of absolute benzene is admixed with a suspension of 7 mmoles (0.02 g) of paraformaldehyde in 10 ml of absolute methanol. The reaction mixture is refluxed for two hours in the presence of a catalytic amount of hydrochloric acid or acetic acid, whereupon the obtained pale-yellow solution is evaporated in vacuo. The residual oily product is triturated with a small amount of acetone to yield the aimed compound in crystalline form in a yield of 89%.

Melting point: 125 to 127 C.° (acetone/ether).

Analysis for $C_{15}H_{21}NO_4$ (279.32): calculated: C 64.50%, H 7.58%, N 5.01%; found: C 64.92%, H 7.14%, N 5.16%.

The corresponding diethoxy analogue can be prepared in an analogous manner, with a yield of 85%.

Melting point: 143 to 147 C.° (ethanol/ether).

Analysis for $C_{17}H_{25}NO_4$ (307.39): calculated: C 66.43%, H 8.20%, N 4.65%; found: C 66.15%, H 8.66%, N 4.68%.

EXAMPLE 2

Preparation of 1-(hydroxymethyl)-4-phenyl-9,10-diethoxy-1,6,7,11b-tetrahydro-2H,4H-[1,3]oxazino[4,3-a]isoquinoline 10 mmoles (2.8 g) of 1-[bis(hydroxymethyl)-methyl]-6,7-diethoxy-1,2,3,4-tetrahydroisoquinoline and 11 mmoles (1.17 g) of freshly distilled benzaldehyde are refluxed in 50 ml of absolute benzene, in the presence of a catalytic amount of hydrochloric acid or acetic acid for 4 hours. The solvent is distilled off and the residual pale-yellow oil is crystallized by trituration with ether. The aimed compound is obtained in a yield of 70%.

Melting point: 94 to 97 C.°

The compounds of the formula (I/1)

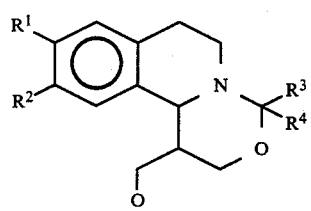

(I/1)

set forth in Table 1 can be prepared in an analogous way, starting from appropriate starting materials.

TABLE 1

| Example | $R^1 = R^2$ | $R^3$ | $R^4$ | Formula Mol. weight | Mp. [C.°] solvent | Analysis [%] calculated | Analysis [%] found | Yield [%] | Ref. Example |
| --- | --- | --- | --- | --- | --- | --- | --- | --- | --- |
| 3 | —$C_2H_5O$ | —$CH_2$—$CH_3$ | H | $C_{19}H_{29}NO_4$ 333.45 | 111–113 ether | C: 68.03 H: 8.71 N: 4.17 | 68.43 9.05 4.10 | 71 | 2 |
| 4 | —$C_2H_5O$ | —CH(CH_3)_2 | H | $C_{20}H_{31}NO_4$ 349.47 | 113–115 benzene/ petroleum ether | C: 68.74 H: 8.94 N: 4.01 | 69.30 8.57 4.18 | 63 | 2 |

TABLE 1-continued

Compounds of formula (I/1)

| Example | $R^1 = R^2$ | $R^3$ | $R^4$ | Formula Mol. weight | Mp. [C.°] solvent | Analysis [%] calculated | found | Yield [%] | Ref. Example |
|---|---|---|---|---|---|---|---|---|---|
| 5 | —C$_2$H$_5$O | 3'-cyclohexenyl | H | C$_{23}$H$_{33}$NO$_4$ 387.50 | 233–234 acetone/ ether | C: 71.28 H: 8.58 N: 3.61 | 71.24 8.89 3.31 | 73 | 2 |
| 6 | —C$_2$H$_5$O | —C$_6$H$_5$ | H | C$_{23}$H$_{29}$NO$_4$ 383.49 | 94–97 ethanol/ ether | C: 72.04 H: 7.62 N: 3.65 | 71.62 7.58 3.54 | 70 | 2 |
| 7 | CH$_3$O | C$_6$H$_5$ | CH$_3$ | C$_{22}$H$_{28}$NO$_4$ 370.45 | 197–201 n. hexane/ acetone | C: 71.32 H: 7.62 N: 3.78 | 71.53 7.39 3.56 | 10 | 3 |
| 8 | CH$_3$O | C$_6$H$_4$OCH$_3$(p) | H | C$_{22}$H$_{27}$NO$_5$ 385.46 | 140–143 ethanol/ ether | C: 68.55 H: 7.06 N: 3.65 | 68.31 6.87 3.52 | 42 | 2 |
| 9 | CH$_3$O | C$_6$H$_2$(OCH$_3$)$_3$ (m.p.m) | H | C$_{24}$H$_{31}$NO$_7$ 445.50 | 202–204 benzene | C: 64.70 H: 7.01 N: 3.14 | 65.06 7.34 3.08 | 90 | 2 |
| 10 | C$_2$H$_5$O | C$_6$H$_2$(OCH$_3$)$_3$ (m.p.m) | H | C$_{26}$H$_{35}$NO$_7$ 473.55 | 214–217 methanol/ ether | C: 65.94 H: 7.45 N: 2.96 | 66.02 7.81 3.28 | 84 | 2 |
| 11 | CH$_3$O | C$_6$H$_4$NO$_2$(p) | H | C$_{21}$H$_{24}$N$_2$O$_6$ 400.44 | 183–186 ethanol/ ether | C: 62.99 H: 6.04 N: 7.00 | 62.57 6.33 6.80 | 70 | 2 |
| 12 | C$_2$H$_5$O | C$_6$H$_4$NO$_2$(p) | H | C$_{23}$H$_{28}$N$_2$O$_6$ 428.49 | 202–203 ethanol | C: 64.47 H: 6.59 N: 6.54 | 64.72 6.91 6.38 | 85 | 2 |
| 13 | CH$_3$O | C$_6$H$_4$Cl(p) | H | C$_{21}$H$_{24}$ClNO$_4$ 389.88 | 160–163 acetone | C: 64.69 H: 6.20 N: 6.59 | 64.31 6.54 6.62 | 90 | 2 |
| 14 | C$_2$H$_5$O | C$_6$H$_4$Cl(p) | H | C$_{23}$H$_{28}$ClNO$_4$ 417.94 | 164–166 ethanol | C: 66.10 H: 6.75 N: 3.35 | 66.60 6.36 3.12 | 83 | 2 |
| 15 | CH$_3$O | C$_6$H$_4$Cl$_2$(m.p) | H | C$_{21}$H$_{23}$Cl$_2$NO$_4$ 424.32 | 157–160 ethanol | C: 59.44 H: 5.46 N: 3.30 | 59.64 5.72 3.11 | 73 | 2 |
| 16 | CH$_3$O | 2-pyridyl | H | C$_{20}$H$_{24}$N$_2$O$_4$ 356.43 | 235–236 ether | C: 67.40 H: 7.79 N: 7.86 | 67.46 7.26 7.77 | 85 | 2 |
| 17 | C$_2$H$_5$O | 2-pyridyl | H | C$_{22}$H$_{28}$N$_2$O$_4$ 384.48 | 228–230 acetone/ ether | C: 68.72 H: 7.34 N: 7.28 | 68.80 7.57 7.81 | 78 | 2 |
| 18 | C$_2$H$_5$O | furyl | H | C$_{21}$H$_{27}$NO$_5$ 373.45 | 97–100 ethanol/ ether | C: 67.52 H: 7.29 | 66.84 7.86 | 57 | 2 |

EXAMPLE 19

Preparation of 1-(hydroxymethyl)-4-(spiro-cyclohexane)-9,10-dimethoxy-1,6,7,11b-tetrahydro-2H,4H-[1,3]oxazino[4,3-a]isoquinoline 0.01 mole (2.7 g) of 1-[bis(hydroxymethyl)-methyl]-6,7-dimethoxy-1,2,3,4-tetrahydroisoquinoline and 0.03 mole (2.9 g) of cyclohexanone are boiled in 100 ml of absolute benzene, in the presence of a catalytic amount of hydrochloric acid or acetic acid for 36 hours, using a water separator. The excess of benzene and cyclohexanone are distilled off in vacuo. The residual yellow oil is crystallized from a mixture of ether and petroleum ether. The aimed compound is obtained in a yield of 49%.

Melting point: 129 to 132 C.°

1-(Hydroxymethyl)-4-methyl-4-phenyl-9,10-dimethoxy-1,6,7,11b-tetrahydro-2H,4H-[1,3]oxazino[4,3-a]isoquinoline can be prepared in an analogous way, using acetophenone as reactant.

Yield: 10%.

Melting point: 197 to 201 C.°

EXAMPLE 20

Preparation of 1-(hydroxymethyl)-9,10-dialkoxy-1,6,7,11b-tetrahydro-2H,4H-[1,3]oxazino[4,3-a]-isoquinoline hydrochlorides The 1-(hydroxymethyl)-9,10-dialkoxy-1,6,7,11b-tetrahydro-2H,4H-[1,3]oxazino[4,3-a]isoquinolines prepared according to Examples 1 to 20 or in an analogous way are dissolved in a solution of hydrochloric acid in absolute ethanol. To the solution obtained absolute ether is added till turbidity, and after storing overnight, the precipitated crystals are filtered off. The yields are nearly quantitative.

The physical and analytical data of the compounds obtained are shown in Table 2.

TABLE 2

HCl salts of compounds of formula (I/1)

| $R^1 = R^2$ | $R^3$ | $R^4$ | Formula Mol. weight | Mp. [C°] Solvent | Analysis [%] calculated | found |
|---|---|---|---|---|---|---|
| CH$_3$O | H | H | C$_{15}$H$_{22}$ClNO$_4$ 315.80 | 129–131 abs. methanol/ ether | C: 57.05 H: 7.02 N: 4.42 | 56.60 7.31 4.61 |

TABLE 2-continued

HCl salts of compounds of formula (I/l)

| $R^1 = R^2$ | $R^3$ | $R^4$ | Formula Mol. weight | Mp. [C°] Solvent | Analysis [%] calculated | found |
|---|---|---|---|---|---|---|
| $C_2H_5O$ | H | H | $C_{17}H_{26}ClNO_4$ 343.85 | 167–170 abs. ethanol/ether | C: 59.38 H: 7.62 N: 4.07 | 59.92 7.79 3.96 |
| $C_2H_5O$ | —$CH_2$—$CH_3$ | H | $C_{19}H_{30}ClNO_4$ 371.91 | 168–174 abs. ethanol/ether | C: 61.36 H: 8.13 N: 3.76 | 61.46 8.67 3.87 |
| $CH_3O$ | —$(CH_2)_3CH_3$ | H | $C_{18}H_{28}ClNO_4$ 357.87 | 147–149 abs. ethanol | C: 60.41 H: 7.88 N: 3.91 | 59.93 7.78 3.83 |
| $C_2H_5O$ | —CH(CH$_3$)$_2$ | H | $C_{20}H_{32}ClNO_4$ 385.93 | 161–165 abs. ethanol | C: 62.24 H: 8.36 N: 3.63 | 62.70 8.29 3.83 |
| $C_2H_5O$ | 3-cyclohexenyl | H | $C_{23}H_{24}ClNO_4$ 423.97 | 162–167 ethanol/ether | C: 65.15 H: 8.08 N: 3.30 | 65.71 8.18 3.01 |
| $CH_3O$ | —$(CH_2)_5$— | | $C_{20}H_{30}ClNO_4$ 383.98 | 202–204 methanol/ether | C: 62.57 H: 7.88 N: 3.65 | 62.16 7.83 4.05 |
| $CH_3O$ | $C_6H_5$ | H | $C_{21}H_{26}ClNO_4$ 391.89 | 197–200 abs. ethanol/ether | C: 64.36 H: 6.69 N: 3.57 | 63.98 7.00 3.27 |
| $C_2H_5O$ | $C_6H_5$ | H | $C_{23}H_{30}ClNO_4$ 419.95 | 184–187 abs. ethanol/ether | C: 65.78 H: 7.20 N: 3.33 | 65.59 7.34 3.20 |
| $CH_3O$ | $C_6H_4CH_3$(p) | H | $C_{22}H_{28}ClNO_4$ 405.93 | 197–199 abs. ethanol/ether | C: 65.10 H: 6.95 N: 3.45 | 64.46 7.46 3.33 |
| $C_2H_5O$ | $C_6H_4CH_3$(p) | H | $C_{24}H_{32}ClNO_4$ 433.98 | 179–182 abs. ethanol/ether | C: 66.42 H: 7.43 N: 3.23 | 66.49 7.57 3.11 |
| $CH_3O$ | $C_6H_4CH_3$(m) | H | $C_{22}H_{28}ClNO_4$ 405.91 | 140–142 abs. ethanol | C: 65.09 H: 6.95 N: 3.45 | 64.94 7.32 3.72 |
| $CH_3O$ | $C_6H_4OCH_3$(p) | H | $C_{22}H_{28}ClNO_5$ 421.93 | 183–185 abs. methanol/ether | C: 62.63 H: 6.69 N: 3.32 | 62.77 6.87 3.45 |
| $C_2H_5O$ | $C_6H_4OCH_3$(p) | H | $C_{24}H_{32}ClNO_5$ 449.98 | 178–180 ethanol/ether | C: 64.06 H: 7.17 N: 3.11 | 63.77 7.15 2.87 |
| $CH_3O$ | $C_6H_4OCH_3$(m) | H | $C_{22}H_{28}ClNO_5$ 421.91 | 164–167 abs. ethanol | C: 62.63 H: 6.69 N: 3.32 | 61.93 7.03 3.82 |
| $CH_3O$ | $C_6H_2(OCH_3)_3$(m,p,m) | H | $C_{24}H_{32}ClNO_7$ 481.97 | 191–192 abs. ethanol | C: 59.80 H: 6.69 N: 2.91 | 58.86 7.20 2.52 |
| $C_2H_5O$ | $C_6H_2(OCH_3)_3$m,p,m | H | $C_{26}H_{36}ClNO_7$ 510.01 | 183–186 abs. ethanol | C: 61.23 H: 7.12 N: 2.75 | 61.21 7.76 2.72 |
| $C_2H_5O$ | $C_6H_4NO_2$(p) | H | $C_{23}H_{29}ClN_2O_6$ 464.95 | 150–153 abs. ethanol | C: 59.42 H: 6.29 N: 6.02 | 59.18 6.62 6.13 |
| $CH_3O$ | $C_6H_4Cl$(p) | H | $C_{21}H_{25}Cl_2NO_4$ 426.34 | 196–199 abs. ethanol/ether | C: 59.16 H: 5.91 N: 3.28 | 58.87 6.00 3.44 |
| $C_2H_5O$ | $C_6H_4Cl$(p) | H | $C_{23}H_{29}Cl_2NO_4$ 454.40 | 162–166 abs. ethanol | C: 60.80 H: 6.43 N: 3.08 | 60.77 6.41 3.59 |
| $CH_3O$ | $C_6H_3Cl_2$(m,p) | H | $C_{21}H_{24}Cl_3NO_4$ 460.78 | 137–140 abs. ethanol | C: 54.74 H: 5.25 N: 3.04 | 55.17 5.78 2.92 |
| $C_2H_5O$ | $C_6H_3Cl_2$(m,p) | H | $C_{23}H_{28}Cl_3NO_4$ 488.83 | 185–189 abs. methanol/ether | C: 56.51 H: 5.77 N: 2.87 | 56.53 6.20 2.24 |
| $CH_3O$ | 2-pyridyl | H | $C_{20}H_{26}Cl_2N_2O_4$ 429.35 | 168–172 acetone/ether | C: 55.95 H: 6.10 N: 6.52 | 55.47 6.59 6.54 |
| $C_2H_5O$ | 2-pyridyl | H | $C_{22}H_{30}Cl_2N_2O_4$ 457.41 | 181–184 ethanol/ether | C: 57.77 H: 6.61 N: 6.12 | 57.23 7.05 5.30 |
| $CH_3O$ | $(CH_2)_2C_6H_5$ | H | $C_{23}H_{30}ClNO_4$ 419.94 | 154–155 abs. ethanol | C: 65.77 N: 3.34 H: 7.20 | 65.79 3.98 7.55 |
| $C_2H_5O$ | $(CH_2)_2C_6H_5$ | H | $C_{25}H_{34}ClNO_4$ 447.98 | 173–176 abs. ethanol | C: 67.02 H: 7.65 | 67.21 7.42 |

TABLE 2-continued

| | | HCl salts of compounds of formula (I/1) | | | |
|---|---|---|---|---|---|
| | | Formula | Mp. [C°] | Analysis [%] | |
| $R^1 = R^2$ | $R^3$ | $R^4$ Mol. weight | Solvent | calculated | found |
| | | | | N: 3.13 | 3.09 |

EXAMPLE 21

Preparation of 1-(chloromethyl)-9,10-diethoxy-1,6,7,11b-tetrahydro-2H,4H-[1,3]oxazino[4,3-a]-isoquinoline hydrochloride 0.01 mole (3.08 g) of 1-(hydroxymethyl)-9,10-diethoxy-1,6,7,11b-tetrahydro-2H,4H-[1,3]oxazino[4,3-a]-isoquinoline is dissolved in 50 ml of absolute benzene. To the solution 0.05 mole (6 g) of sulfinyl dichloride is added dropwise, under ice cooling and stirring. Thereafter the reaction mixture is slightly refluxed for 3 hours. The excess of the solvent and sulfinyl dichloride is distilled off in vacuo. The residual brown oil is triturated with a small amount of ether to yield the desired compound in crystalline form in a yield of 37%.

Melting point: 149 to 153 C.° (ethanol/ether).

Analysis for $C_{17}H_{21}Cl_2NO_3$ (362.30): calculated: C 56.36%, H 6.98%, N 3.86%; found: C 56.38%, H 6.64%, N 3.62%.

EXAMPLE 22

Preparation of 1-(hydroxymethyl)-9,10-dimethoxy-1,6,7,11b-tetrahydro-2H,4H-[1,3]oxazino-[4,3-a]isoquinoline 6 mmoles (1.6 g) of 1-[bis(hydroxymethyl)-methyl]-6,7-dimethoxy-1,2,3,4-tetrahydroisoquinoline are stirred with 10 ml of aqueous (30–35%) formaldehyde for half an hour. The reaction mixture is alkalized with 10 ml of a 30% aqueous sodium hydroxide solution and extracted with ethyl acetate. Drying and evaporation of the extract yields the aimed compound in a yield of 89%.

Melting point: 126 to 127 C° (acetone/ether).

The product does not give any melting point depression when admixed with the product of Example 1.

EXAMPLE 23

Preparation of 1-(hydroxymethyl)-4-phenyl-9,10-diethoxy-1,6,7,11b-tetrahydro-2H,4H-[1,3-a]-oxazino[4,3-a]isoquinoline 5 mmoles (1.47 g) of 1-[bis(hydroxymethyl)-methyl]-6,7-diethoxy-1,2,3,4-tetrahydroisoquinoline and 5.5 mmoles (0.84 g) of benzaldehyde dimethylacetal are boiled in 50 ml of ethanol. Ring closure is catalysed by adding a drop of ethanolic hydrochloric acid or acetic acid. When the reaction is complete (4 to 6 hours), the solvent is distilled off and the obtained pale-yellow oil is crystallized by trituration with ether.

Yield: 56%.

Melting point: 93 to 96 C°.

The compound obtained does not give any melting point depression when admixed with the product of Example 6.

EXAMPLE 24

Preparation of 1-(hydroxymethyl)-4-phenyl-9,10-diethoxy-1,6,7,11b-tetrahydro-2H,4H-[1,3]-oxazino[4,3-a]isoquinoline Following the procedure described in Example 23, using 5.5 mmoles of benzaldehyde the aimed compound is obtained in a yield of 47%.

Melting point: 93 to 95 C°.

The compound obtained does not give any melting point depression when admixed with the product of Example 6 or Example 23.

EXAMPLE 25

Preparation of 1-(benzoyloxymethyl)-9,10-dimethoxy-1,6,7,11b-tetrahydro-2H,4H-[1,3]-oxazino[4,3-a]isoquinoline 0.01 mole (4.08 g) of 1-[1'-(benzoyloxymethyl)-1'-(hydroxymethyl)-methyl]-6,7-dimethoxy-1,2,3,4-tetrahydroisoquinoline in 30 ml of a 36% aqueous formaldehyde solution is stirred at room temperature for 4 hours. The reaction mixture is evaporated to dryness and the residue is crystallized from a mixture of acetone and ether.

Yield: 82%.

Melting point: 142 to 143 C.° (diisopropyl ether/ethanol).

Analysis for $C_{18}H_{29}NO_5$ (459.52): calculated: C 73.18%, H 6.36%, N 3.05%; found: C 73.00%, H 6.23%, N 2.68%.

EXAMPLE 26

Preparation of 1-(benzoyloxymethyl)-9,10-dimethoxy-1,6,7,11b-tetrahydro-2H,4H-[1,3]oxazino-[4,3-a]isoquinoline 0.01 mole (2.79 g) of 1-(hydroxymethyl)-9,10-dimethoxy-1,6,7,11b-tetrahydro-2H,4H-[1,3]oxazino[4,3-a]isoquinoline in 30 ml of absolute pyridine is boiled with 0.012 mole (1.69 g) of benzoyl chloride for 3 hours. The mixture is then poured onto 100 g of ice. The separated crystals are filtered off, washed with water and recrystallized from a mixture of diisopropyl ether and ethanol. Yield: 55%. The melting point and spectroscopical data of the compound are identical with those of the product obtained in Example 25.

EXAMPLE 27

Preparation of 1-(hydroxymethyl)-9,10-dimethoxy-1,6,7,11b-tetrahydro-2H,4H-[1,3]oxazino[4,3-a]-isoquinoline 0.01 mole (2.67 g) of 1-[bis(hydroxymethyl)-methyl]-6,7-dimethoxy-1,2,3,4-tetrahydroisoquinoline is dissolved in 30 ml of ethanol, and the solution is stirred with 0.015 mole of acetaldehyde for one hour. The reaction mixture is evaporated to dryness to yield the aimed compound in a crystalline form.

Melting point: 140 to 141 C.° (ethyl acetate).

Analysis for $C_{16}H_{23}NO_4$ (293.35): calculated: C 65.50%, H 7.90%, N 4.78%; found: C 65.42%, H 7.86%, N 4.90%.

We claim:

1. oxazinoisoquinoline derivatives of the formula (I)

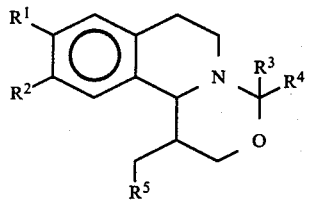

(I)

wherein $R^1$ and $R^2$ represent hydroxyl or alkoxy having from 1 to 6 carbon atoms, $R^3$ is hydrogen, alkyl having from 1 to 8 carbon atoms, cycloalkyl or cycloalkenyl having from 3 to 6 carbon atoms, phenyl, phenyl substituted by halogen, alkoxy of 1–4 carbons or nitro, $C_1$–$C_4$-alkyl phenyl or heteroaryl, $R^4$ is hydrogen or alkyl having from 1 to 4 carbon atoms, or $R^3$ and $R^4$ together form a —(CH$_2$)$_n$— group, in which n is an integer from 3 to 7, $R^5$ is hydroxyl, halogen or an

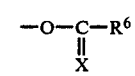

group, in which
$R^6$ is phenyl,
X is oxygen or sulfur,
and salts thereof.

2. A derivative of the formula (I) of claim 1, wherein heteroaryl is pyridyl or furyl.

3. A derivative of the formula (I) of claim 1, wherein $R^3$ is benzyl or phenylethyl.

4. The derivative as defined in claim 1, which is 1-(hydroxymethyl)-4-(4-pyridyl)-8,10-diethoxy-1,6,7,11b-tetrahydro-2H,4H-oxazinoisoquinoline dihydrochloride.

5. The derivative as defined in claim 1, which is 1-(hydroxymethyl)-4-(phenylethyl)-9,10-dimethoxy-1,6,7,11b-tetrahydro-2H,4H oxazino-isoquinoline hydrochloride.

6. A pharmaceutical composition comprising as active ingredient an effective amount of at least one compound of formula (I), as defined in claim 1, or a physiologically acceptable salt thereof, in association with a pharmaceutical carrier and/or excipient.

7. A method of lessening pain which comprises: treating a patient with an effective amount of a composition as defined in claim 6.

* * * * *